(12) United States Patent
Yuan et al.

(10) Patent No.: US 9,655,875 B2
(45) Date of Patent: May 23, 2017

(54) METHOD OF TREATING OR PREVENTING TUMORS USING 1-(ALKYLSULFINYL)-2-ISOTHIOCYANATOALKYL-1-ALKENE

(71) Applicant: BEIJING UNIVERSITY OF CHEMICAL TECHNOLOGY, Beijing (CN)

(72) Inventors: Qipeng Yuan, Beijing (CN); Ming Yang, Beijing (CN); Hao Liang, Beijing (CN)

(73) Assignee: BEIJING UNIVERSITY OF CHEMICAL TECHNOLOGY, Beijing (CN)

( * ) Notice: Subject to any disclaimer, the term of this patent is extended or adjusted under 35 U.S.C. 154(b) by 0 days.

(21) Appl. No.: 15/093,810

(22) Filed: Apr. 8, 2016

(65) Prior Publication Data

US 2016/0220526 A1 Aug. 4, 2016

Related U.S. Application Data

(63) Continuation-in-part of application No. PCT/CN2013/084832, filed on Oct. 8, 2013.

(51) Int. Cl.
*A61K 31/26* (2006.01)
*A61K 36/31* (2006.01)
*A23L 33/00* (2016.01)
*A23L 33/105* (2016.01)

(52) U.S. Cl.
CPC ............ *A61K 31/26* (2013.01); *A23L 33/105* (2016.08); *A23L 33/30* (2016.08); *A61K 36/31* (2013.01); *A23V 2002/00* (2013.01)

(58) Field of Classification Search
CPC ......... A61K 31/26; A61K 36/31; A23L 33/30; A23L 33/105
USPC ....................................................... 514/514
See application file for complete search history.

(56) References Cited

PUBLICATIONS

Papi et al. Journal of Agricultural and Food Chemistry, 2008, 56, 875-883.*

* cited by examiner

*Primary Examiner* — Yevegeny Valenrod
(74) *Attorney, Agent, or Firm* — Matthias Scholl, PC; Matthias Scholl

(57) ABSTRACT

A method of treating or preventing human or mammalian cancer and tumor including administering to a patient or an animal in need thereof a pharmaceutical composition, a health product, or a food additive, including 1-(alkylsulfinyl)-2-isothiocyanatoalkyl-1-alkene.

13 Claims, 5 Drawing Sheets

Antitumor experiment against carcinoma cells H460 xenograft

METHOD OF TREATING OR PREVENTING TUMORS USING 1-(ALKYLSULFINYL)-2-ISOTHIOCYANATOALKYL-1-ALKENE

CROSS-REFERENCE TO RELATED APPLICATIONS

This application is a continuation-in-part of International Patent Application No. PCT/CN2013/084832 with an international filing date of Oct. 8, 2013, designating the United States, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, and Cambridge, Mass. 02142.

BACKGROUND OF THE INVENTION

Field of the Invention

The invention relates to use of 1-(alkylsulfinyl)-2-isothiocyanatoalkyl-1-alkene for treating or preventing human or mammalian cancers and tumors.

Description of the Related Art

The antitumor activity of 1-(alkylsulfinyl)-2-isothiocyanatoalkyl-1-alkene has not been reported heretofore.

SUMMARY OF THE INVENTION

Unexpectedly, the inventors found sulforaphene is superior to conventional antitumor drugs including sulforaphane, erlotinib, gemcitabine and paclitaxel in inhibiting the growth of many kinds of cancer cells, and has higher security than sulforaphane, cis-platinum, 5-fluorouraeil, paclitaxel, and adriamycin. So, sulforaphene has potential antitumor activities against lung cancer, lung squamous cell carcinoma, pancreas cancer, liver cancer, mammary cancer, cervical carcinoma, malignant melanoma, and so on.

In view of the above-described findings, in accordance with one embodiment of the invention, there is provided a method of treating or preventing human or mammalian cancer and tumor comprising administering to a patient or an animal in need thereof a pharmaceutical composition, health product, or food additive comprising 1-(alkylsulfinyl)-2-isothiocyanatoalkyl-1-alkene having the formula I wherein $R_1$ is a methyl; $R_2$ and $R_3$ at each occurrence independently represent a substituted or unsubstituted alkyl, vinyl, alkynyl, aryl, alkoxy, epoxy group, heterocyclic nitrogen and aryloxy; $R_4$ is a substituted or unsubstituted alkylidene, —$CH_2$—O—$CH_2$—, and alkoxyl aryl; and n is an integer from 1 to 10. Preferably, n is an integer from 1 to 5, and more preferably, n is 2. The double bond in $R_2$—$C_1$=$C_2$—$R_3$ is a cis-structure or a trans-structure.

The invention also provides a method of treating or preventing human or mammalian cancer and tumor comprising administering to a patient or an animal in need thereof 4-isothiocyanato-1-(methylsulfinyl)-1-butene having the formula II Sulforaphene is a member of the family of isothiocyanate. Sulforaphane, that is, 1-isothiocyanato-4-(methysulfinyl)-butane, has the formula III The difference between sulforaphene and sulforaphane is that the former has an unsaturated C=C bond at the alpha carbon position.

In a class of this embodiment, sulforaphene is extracted from radish seeds, radish seedlings, or radish.

In a class of this embodiment, the pharmaceutical composition, health product, and food additive comprise a pharmaceutically acceptable carrier, an additive, and a pharmaceutically acceptable excipient.

In a class of this embodiment, the human or mammalian cancer and tumor comprise lung cancer, gastric cancer, colon cancer, rectal cancer, ovarian cancer, mammary cancer, thyroid cancer, pancreas cancer, esophageal cancer, head and neck cancer, cervical carcinoma, endometrial carcinoma, malignant melanoma, and bladder cancer.

Specifically, sulforaphene having the formula II in the invention is a medicinal compound and extracted from *Brassica* plants including but not limited to radish, broccoli, cabbage, mustard and horseradish. The compound has effective treatment and prevention for the abovementioned cancers and tumors.

Sulforaphene of the invention can also be prepared as food, additives and health products for the treatment and prevention of the cancers and tumors.

Based on a series of in vitro anti-cancer experiments against A549 cell line, the inventors found that sulforaphene exhibits stronger inhibition than sulforaphane against the growth and proliferation of human lung adenocarcinoma cells. Experiments showed that, when subjects were administered with sulforaphene and sulforaphane, respectively, with different administration concentrations (for example, the administration concentrations of the two compounds are 10, 20, 30, 40, and 50 μM), 48 hours later, calculation results show the half maximal inhibitory concentration (IC50) of sulforaphene against human lung adenocarcinoma cells A549 is 10.5 μM, and the IC50 of sulforaphane is 14.7 μM.

Based on a series of in vitro anti-cancer experiments against H460 cell line, the inventors found that sulforaphene exhibits stronger inhibition than sulforaphane against the growth and proliferation of human lung squamous carcinoma cells. Experiments showed that, when subjects were administered with sulforaphene and sulforaphane, respectively, with different administration concentrations (for example, the administration concentrations of the two compounds are 10, 20, 30, 40, and 50 μM), 48 hours later, calculation results show the half maximal inhibitory concentration (IC50) of sulforaphene against human lung squamous carcinoma cells H460 is 25.7 μM, and the IC50 of sulforaphane is 34.62 μM.

Based on a series of in vitro anti-cancer experiments against PANC-1 cell line, the inventors found that sulforaphene exhibits stronger inhibition than sulforaphane against the growth and proliferation of human pancreatic cancer cells. Experiments showed that, when subjects were administered with sulforaphene and sulforaphane, respectively, with different administration concentrations (for example, the administration concentrations of the two compounds are 10, 20, 30, 40, and 50 μM), 48 hours later, calculation results show the half maximal inhibitory concentration (IC50) of sulforaphene against human pancreatic cancer cells PANC-1 is 5.18 μM, and the IC50 of sulforaphane is 6.73 μM.

Based on a series of in vitro anti-cancer experiments against MCF-7 cell line, the inventors found that sulforaphene exhibits stronger inhibition than sulforaphane against the growth and proliferation of human breast cancer cells. Experiments showed that, when subjects were administered with sulforaphene and sulforaphane, respectively, with different administration concentrations (for example, the administration concentrations of the two compounds are 10, 20, 30, 40, and 50 μM), 48 hours later, calculation results show the half maximal inhibitory concentration (IC50) of sulforaphene against human breast cancer cells MCF-7 is 14.3 μM, and the IC50 of sulforaphane is 19.46 μM.

Based on a series of in vitro anti-cancer experiments against HepG2 cell line, the inventors found that sulforaphene exhibits stronger inhibition than sulforaphane against the growth and proliferation of human liver cancer cells. Experiments showed that, when subjects were administered with sulforaphene and sulforaphane, respectively, with different administration concentrations (for example, the administration concentrations of the two compounds are 10, 20, 30, 40, and 50 μM), 48 hours later, calculation results show the half maximal inhibitory concentration (IC50) of sulforaphene against human liver cancer cells HepG2 is 59.0 μM, and the IC50 of sulforaphane is 47.33 μM.

Based on a series of in vitro anti-cancer experiments against HeLa cell line, the inventors found that sulforaphene exhibits stronger inhibition than sulforaphane against the growth and proliferation of human cervical cancer cells. Experiments showed that, when subjects were administered with sulforaphene and sulforaphane, respectively, with different administration concentrations (for example, the administration concentrations of the two compounds are 10, 20, 30, 40, and 50 μM), 48 hours later, calculation results show the half maximal inhibitory concentration (IC50) of sulforaphene against human cervical cancer cells HeLa is 24.1 μM, and the IC50 of sulforaphane is 25.8 μM.

Based on a series of in vitro anti-cancer experiments against A375 cell line, the inventors found that sulforaphene exhibits stronger inhibition than sulforaphane against the growth and proliferation of human malignant melanoma cancer cells. Experiments showed that, when subjects were administered with sulforaphene and sulforaphane, respectively, with different administration concentrations (for example, the administration concentrations of the two compounds are 10, 20, 30, 40, and 50 μM), 48 hours later, calculation results show the half maximal inhibitory concentration (IC50) of sulforaphene against human malignant melanoma cancer cells A375 is 26.088 μM, and the IC50 of sulforaphane is 33.11 μM.

Based on a series of in vitro anti-cancer experiments against A549 and H460 cell line, the inventors found that sulforaphene exhibits stronger inhibition against the growth and proliferation of human lung cancer cells compared with erlotinib, gemcitabine and paclitaxel.

Based on a series of in vitro anti-cancer experiments against MCF-7 cell line, the inventors found that sulforaphene exhibits stronger inhibition against the growth and proliferation of human cancer cells compared with erlotinib and gemcitabine, but the activity is slightly lower than that of paclitaxel.

Based on cytotoxicity tests of peripheral blood mononuclear cells, the results show the cytotoxicity of sulforaphene against leukocyte is significantly lower than that of sulforaphane, cis-platinum, 5-fluorouraeil, paclitaxel, and adriamycin. Further cytotoxicity tests of rat myocardial cells show that, the cytotoxicity of sulforaphene is significantly lower than that of sulforaphane and adriamycin.

The experiment subjects of the pharmaceutical composition comprising sulforaphene can be human beings, primates and other mammals. The administration mode can be oral administration, nasal administration, parenteral administration, or external use (for example, drops or transdermal patches). The term "parenteral administration" includes intravenous injection, intramuscular injection, sternum injection, hypodermic injection, and intra-articular injection.

The pharmaceutical composition comprising sulforaphene can be a solid, such as tablets, sugar-coated tablets, pills, capsules, granules, or microgranules (including powders or small-sized packings). A solid preparation of the pharmaceutical composition can be obtained by mixing pharmaceutically acceptable inert ingredients and the solid sulforaphene.

The dosage form of the pharmaceutical composition comprising sulforaphene can be oral liquid, which includes but is not limited to pharmaceutically acceptable emulsions, solutions, suspensions, syrups, and elixirs. Besides sulforaphene, the liquid dosage form can include an inert diluent, such as water, solubilizer and emulsifier. The inert diluent can further include an adjuvant, such as wetting agent, emulsifier, and suspending agent, sweeteners, taste masking agent, and fragrances.

The dosage form of the pharmaceutical composition comprising sulforaphene can be injections, which include and are not limited to emulsions and solutions.

The dosage form of the pharmaceutical composition comprising sulforaphene can be suspensions, which are isostearyl alcohol, polysorbitolum, sorbitan, microcrystalline cellulose, bentonite, agar, tragacanth gum, or a mixture thereof.

The pharmaceutical composition comprising sulforaphene of the invention can be administered in the form of liposome which is derived from phospholipids and other lipids. Liposome is a specific preparation in which the active ingredients are coated by vesicles which are originated from lipid bilayer membrane. Liposome can act as a carrier for nutrients and drugs. Liposome can be prepared by destroying biomembranes, for example, by ultrasonic processing.

The pharmaceutical composition comprising 1-(alkylsulfinyl)-2-isothiocyanatoalkyl-1-alkene of the invention can also comprises one or more pharmaceutically acceptable carriers, additives, and pharmaceutically acceptable excipients. The pharmaceutically acceptable carriers are 8-[(2-hydroxy-4-methoxy benzoyl) amino]-octanoic sodium, as disclosed in U.S. Pat. No. 5,650,386, which can be used following the teaching in the literature. The additives can be Vitamin A or C. The excipients include but are not limited to solid or liquid.

DETAILED DESCRIPTION OF THE EMBODIMENTS

For further illustrating the invention, experiments detailing use of 1-(alkylsulfinyl)-2-isothiocyanatoalkyl-1-alkene for treating or preventing human or mammalian cancers and tumors are described below. It should be noted that the following examples are intended to describe and not to limit the invention.

I. Growth Inhibition of Human Cancer Cells In Vitro

Preparation of sulforaphene: glucosinolates in pre-ground radish seeds were hydrolyzed by an endogenous myrosinase in a phosphate buffer solution (PBS) having a pH value of 7 at the room temperature. In order to remove proteins and other impurities, the pH value was regulated to be 2.0, and a resulting solution was filtered, extracted, and dried to obtain a natural crude extract, and sulforaphene having a purity of larger than 98 wt. % was yielded by a high-speed counter-current chromatography (HSCCC).

General operations: human cancer cells are cultured in a RPMI-1640 (HyClone) culture medium comprising 10 v. % of a fetal bovine serum (FBS), and the culture medium is then placed in an incubator (37° C., 5% $CO_2$) for 24 hrs. A 0.25% trypsin solution and 0.02% EDTA solution are utilized after cell proliferation for common digestion and subculture. The EDTA solution is a traditional digestion mean. Trypsin is a serine protease possessing substrate specificity and used to digest adherent cells. However, divalent cations, such as calcium ions and magnesium ions, exist in the cells and are able to inhibit the digestion. EDTA is used to chelate these divalent cations so as to enhance the digestion effect of the trypsin. MTT assay is commonly used to measure the cell proliferation, the percentage of viable cells, and the cytotoxicity. MTT (3-(4,5-dimethylthiazol-2-yl)-2,5-diphenyltetrazolium bromide) (also called thiazolyl blue tetrazolium bromide) is a kind of yellow dye. The principle of the MTT assay is that the succinate dehydrogenase in mitochondria of living cells is capable of reducing the exogenous MTT into water-insoluble blue-purple crystalline formazan, which forms a precipitate in the cells, while dead cells do not have such function. Dimethyl sulfoxide (DMSO) dissolves formazan in cells. The absorbance measured at a 490 nm wavelength using an enzyme-linked immunosorbent assay indirectly represents the number of viable cells. In a certain range of the cell numbers, the amount of the formed MTT crystals is in positive proportion to the cell number. Thus, the MTT assay is used to evaluate and determine the survival rate or the inhibition rate of the cells. Such method has been widely applied in activity detection of some bioactive factors, large scale screen of antitumor drugs, cytotoxicity test, and determination of tumor radiosensity and features high sensibility.

Specific embodiments of the invention are described hereinbelow for further explaining the advantages of the invention, however, the following embodiments should not be considered as limitations of the protection scope of any or all of the claims.

Example 1

Materials and Methods

1. Experimental cell lines and related chemical reagents: human lung adenocarcinoma cell line A549 purchased from US ATCC cell bank was cultured in the RPMI-1640 (HyClone) culture medium comprising 10 v. % of the FBS, digested by the 0.25% trypsin solution and 0.02% EDTA solution, and then subcultured. All related chemical reagents in this experiment were purchased from Sigma.

2. Inhibition of A549 cells in vitro by sulforaphene and sulforaphane: A549 cells at exponential growth phase were collected, digested into single cells, and inoculated to 96-well plates with each hole containing 3000 cells. Then the 96-well plates were transferred into an incubator (37° C., 5% $CO_2$) for culture. Sulforaphene and sulforaphane were respectively dissolved by sterile deionized water, resulting solutions were then allowed to pass through 0.22 μM filters for removing bacteria. Filtrates were then diluted by a serum-containing medium to enable final concentrations of the sulforaphene or sulforaphane to be 10 μM, 20 μM, 30 μM, 40 μM, and 50 μM, respectively. After 24 hrs of cultivation, the A549 cells were then cultured by the culture solutions comprising the sulforaphene or sulforaphane of corresponding concentrations, and to the culture media of the negative control group an equal volume of sterile deionized water was added for cell culture. After another 48 hrs of cultivation, 20 μL of MTT was added to each hole, and the plates were incubated for 3 hrs in the incubator (37° C., 5% $CO_2$). Solution in each hole was then removed and replaced by 150 μL of DMSO. Thereafter, the plates were cultured in a shaking table for 10 min, and the absorbance of each hole was measured at the wavelength of 490 nm. The number of viable cells in the negative control group at 0 hr was taken as a basis, and a 50% inhibitory concentration (IC 50) on the cell growth was calculated. The experiment results were listed in FIG. 1.

Experiment Results

Figure 1:
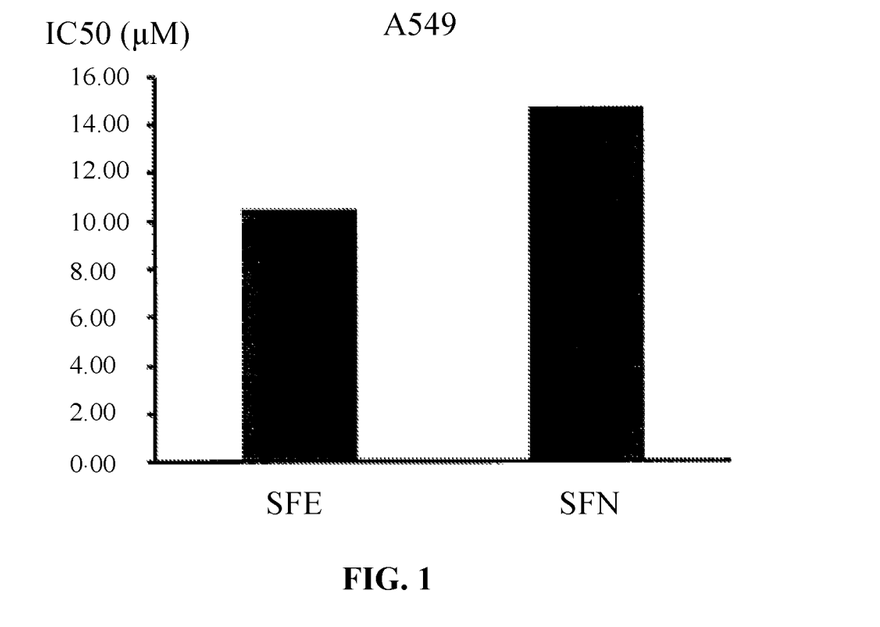
FIG. 1 shows comparison graphs of the half maximal inhibitory concentration (IC50) of sulforaphene and sulforaphane against human lung adenocarcinoma cells A549.

It was indicated from FIG. 1 that sulforaphene has significant inhibition effect on the growth and proliferation of the human lung adenocarcinoma cells A549. After 48 hrs of treatment, the IC50 of sulforaphene on the growth of the A549 cells was 10.5 µM. Sulforaphane has significant inhibition effect on the growth and proliferation of the human lung adenocarcinoma cells A549. After 48 hrs of treatment, the IC50 of sulforaphane on the growth of the A549 cells was 14.7 µM.

Example 2

Materials and Methods

1. Experimental cell lines and related chemical reagents: human lung squamous carcinoma cell line H460 purchased from US ATCC cell bank was cultured in the RPMI-1640 (HyClone) culture medium comprising 10 v. % of the FBS, digested by the 0.25% trypsin solution and 0.02% EDTA solution, and then subcultured. All related chemical reagents in this experiment were purchased from Sigma.

2. Inhibition of H460 cells in vitro by sulforaphene and sulforaphane: H460 cells at exponential growth phase were collected, digested into single cells, and inoculated to 96-well plates with each hole containing 3000 cells. Then the 96-well plates were transferred into an incubator (37° C., 5% $CO_2$) for culture. Sulforaphene and sulforaphane were respectively dissolved by sterile deionized water, resulting solutions were then allowed to pass through 0.22 µM filters for removing bacteria. Filtrates were then diluted by a serum-containing medium to enable final concentrations of the sulforaphene or sulforaphane to be 10 µM, 20 µM, 30 µM, 40 µM, and 50 µM, respectively. After 24 hrs of cultivation, the H460 cells were then cultured by the culture solutions comprising the sulforaphene or sulforaphane of corresponding concentrations, and to the culture media of the negative control group an equal volume of sterile deionized water was added for cell culture. After another 48 hrs of cultivation, 20 µL of MTT was added to each hole, and the plates were incubated for 3 hrs in the incubator (37° C., 5% $CO_2$). Solution in each hole was then removed and replaced by 150 µL of DMSO. Thereafter, the plates were cultured in a shaking table for 10 min, and the absorbance of each hole was measured at the wavelength of 490 nm. The number of viable cells in the negative control group at 0 hr was taken as a basis, and the IC 50 on the cell growth was calculated. The experiment results were listed in FIG. 2.

Experiment Results

Figure 2:
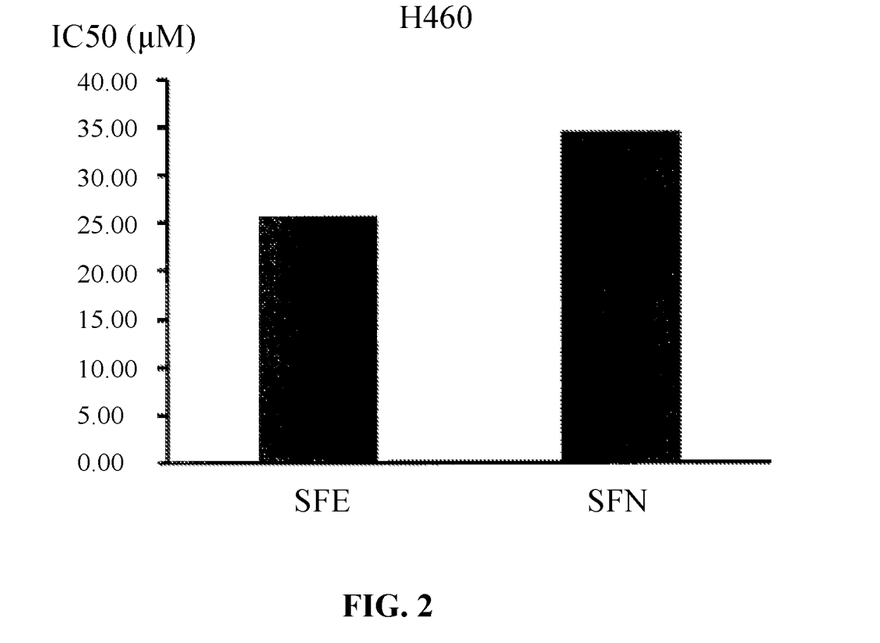
FIG. 2 shows comparison graphs of the half maximal inhibitory concentration (IC50) of sulforaphene and sulforaphane against human lung squamous carcinoma cells H460.

It was indicated from FIG. 2 that sulforaphene has significant inhibition effect on the growth and proliferation of the human lung squamous carcinoma cells H460. After 48 hrs of treatment, the IC50 of sulforaphene on the growth of the H460 cells was 25.7 µM. Sulforaphane has significant inhibition effect on the growth and proliferation of the human lung squamous carcinoma cells H460. After 48 hrs of treatment, the IC50 of sulforaphane on the growth of the H460 cells was 34.62 µM.

Example 3

Materials and Methods

1. Experimental cell lines and related chemical reagents: human pancreatic carcinoma cell line PANC-I purchased from US ATCC cell bank was cultured in the RPMI-1640 (HyClone) culture medium comprising 10 v. % of the FBS, digested by the 0.25% trypsin solution and 0.02% EDTA solution, and then subcultured. All related chemical reagents in this experiment were purchased from Sigma.

2. Inhibition of PANC-I cells in vitro by sulforaphene and sulforaphane: PANC-I cells at exponential growth phase were collected, digested into single cells, and inoculated to 96-well plates with each hole containing 3000 cells. Then the 96-well plates were transferred into an incubator (37° C., 5% $CO_2$) for culture. Sulforaphene and sulforaphane were respectively dissolved by sterile deionized water, resulting solutions were then allowed to pass through 0.22 µM filters for removing bacteria. Filtrates were then diluted by a serum-containing medium to enable final concentrations of the sulforaphene or sulforaphane to be 10 µM, 20 µM, 30 µM, 40 µM, and 50 µM, respectively. After 24 hrs of cultivation, the PANC-I cells were then cultured by the culture solutions comprising the sulforaphene or sulforaphane of corresponding concentrations, and to the culture media of the negative control group an equal volume of sterile deionized water was added for cell culture. After another 48 hrs of cultivation, 20 µL of MTT was added to each hole, and the plates were incubated for 3 hrs in the incubator (37° C., 5% $CO_2$). Solution in each hole was then removed and replaced by 150 µL of DMSO. Thereafter, the plates were cultured in a shaking table for 10 min, and the absorbance of each hole was measured at the wavelength of 490 nm. The number of viable cells in the negative control group at 0 hr was taken as a basis, and the IC 50 on the cell growth was calculated. The experiment results were listed in FIG. 3.

Experiment Results

Figure 3:
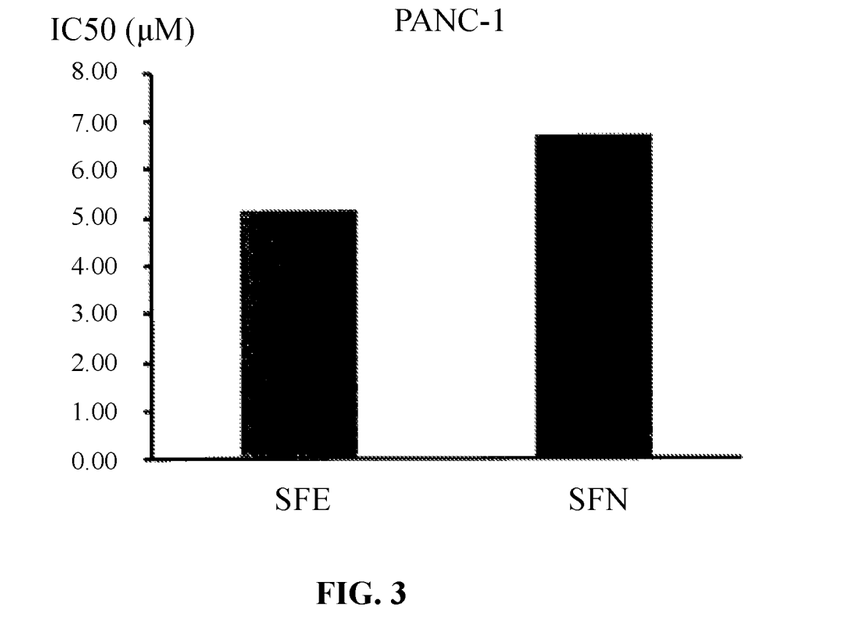
FIG. 3 shows comparison graphs of the half maximal inhibitory concentration (IC50) of sulforaphene and sulforaphane against human pancreatic cancer cells PANC-1.

It was indicated from FIG. 3 that sulforaphene has significant inhibition effect on the growth and proliferation of the human pancreatic carcinoma cells PANC-I. After 48 hrs of treatment, the IC50 of sulforaphene on the growth of the PANC-I cells was 5.18 µM. Sulforaphane has significant inhibition effect on the growth and proliferation of the human pancreatic carcinoma cells PANC-I. After 48 hrs of treatment, the IC50 of sulforaphane on the growth of the PANC-I cells was 6.73 µM.

Example 4

Materials and Methods

1. Experimental cell lines and related chemical reagents: human breast carcinoma cell line MCF-7 purchased from US ATCC cell bank was cultured in the RPMI-1640 (HyClone) culture medium comprising 10 v. % of the FBS, digested by the 0.25% trypsin solution and 0.02% EDTA solution, and then subcultured. All related chemical reagents in this experiment were purchased from Sigma.

2. Inhibition of MCF-7 cells in vitro by sulforaphene and sulforaphane: MCF-7 cells at exponential growth phase were collected, digested into single cells, and inoculated to 96-well plates with each hole containing 3000 cells. Then the 96-well plates were transferred into an incubator (37° C., 5% $CO_2$) for culture. Sulforaphene and sulforaphane were respectively dissolved by sterile deionized water, resulting solutions were then allowed to pass through 0.22 µM filters for removing bacteria. Filtrates were then diluted by a serum-containing medium to enable final concentrations of the sulforaphene or sulforaphane to be 10 µM, 20 µM, 30 µM, 40 µM, and 50 µM, respectively. After 24 hrs of cultivation, the MCF-7 cells were then cultured by the culture solutions comprising the sulforaphene or sulforaphane of corresponding concentrations, and to the culture media of the negative control group an equal volume of sterile deionized water was added for cell culture. After another 48 hrs of cultivation, 20 µL of MTT was added to each hole, and the plates were incubated for 3 hrs in the incubator (37° C., 5% $CO_2$). Solution in each hole was then removed and replaced by 150 μL of DMSO. Thereafter, the plates were cultured in a shaking table for 10 min, and the absorbance of each hole was measured at the wavelength of 490 nm. The number of viable cells in the negative control group at 0 hr was taken as a basis, and the IC 50 on the cell growth was calculated. The experiment results were listed in FIG. 4.

Experiment Results

Figure 4:
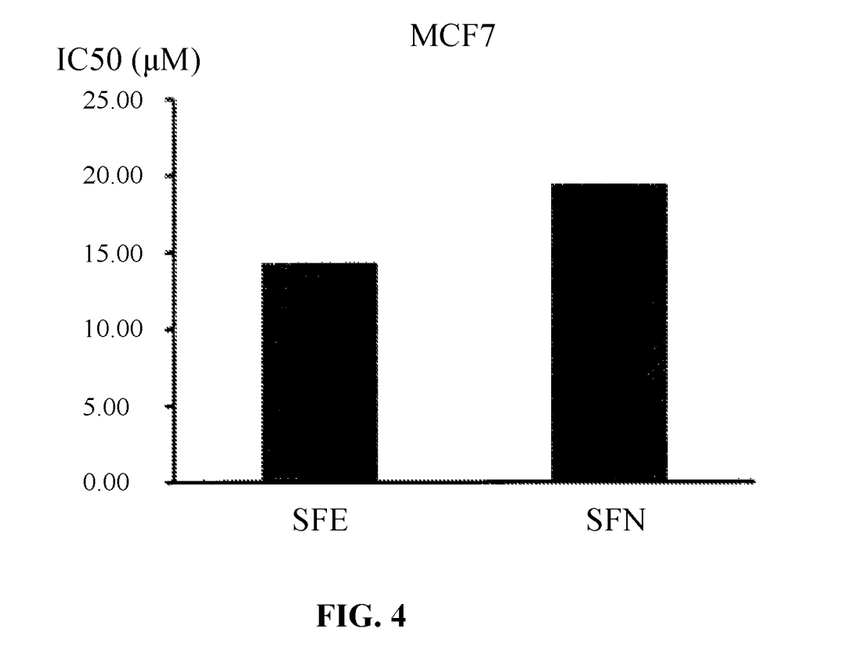
FIG. 4 shows comparison graphs of the half maximal inhibitory concentration (IC50) of sulforaphene and sulforaphane against human breast cancer cells MCF-7.

It was indicated from FIG. 4 that sulforaphene has significant inhibition effect on the growth and proliferation of the human breast carcinoma cells MCF-7. After 48 hrs of treatment, the IC50 of sulforaphene on the growth of the MCF-7 cells was 14.3 μM. Sulforaphane has significant inhibition effect on the growth and proliferation of the human breast carcinoma cells MCF-7. After 48 hrs of treatment, the IC50 of sulforaphane on the growth of the MCF-7 cells was 19.46 μM.

Example 5

Materials and Methods

1. Experimental cell lines and related chemical reagents: human hepatocarcinoma cell line HepG2 purchased from US ATCC cell bank was cultured in the RPMI-1640 (Hy-Clone) culture medium comprising 10 v. % of the FBS, digested by the 0.25% trypsin solution and 0.02% EDTA solution, and then subcultured. All related chemical reagents in this experiment were purchased from Sigma.

2. Inhibition of HepG2 cells in vitro by sulforaphene and sulforaphane: HepG2 cells at exponential growth phase were collected, digested into single cells, and inoculated to 96-well plates with each hole containing 3000 cells. Then the 96-well plates were transferred into an incubator (37° C., 5% $CO_2$) for culture. Sulforaphene and sulforaphane were respectively dissolved by sterile deionized water, resulting solutions were then allowed to pass through 0.22 μM filters for removing bacteria. Filtrates were then diluted by a serum-containing medium to enable final concentrations of the sulforaphene or sulforaphane to be 10 μM, 20 μM, 30 μM, 40 μM, and 50 μM, respectively. After 24 hrs of cultivation, the HepG2 cells were then cultured by the culture solutions comprising the sulforaphene or sulforaphane of corresponding concentrations, and to the culture media of the negative control group an equal volume of sterile deionized water was added for cell culture. After another 48 hrs of cultivation, 20 μL of MTT was added to each hole, and the plates were incubated for 3 hrs in the incubator (37° C., 5% $CO_2$). Solution in each hole was then removed and replaced by 150 μL of DMSO. Thereafter, the plates were cultured in a shaking table for 10 min, and the absorbance of each hole was measured at the wavelength of 490 nm. The number of viable cells in the negative control group at 0 hr was taken as a basis, and the IC 50 on the cell growth was calculated. The experiment results were listed in FIG. 5.

Experiment Results

Figure 5:
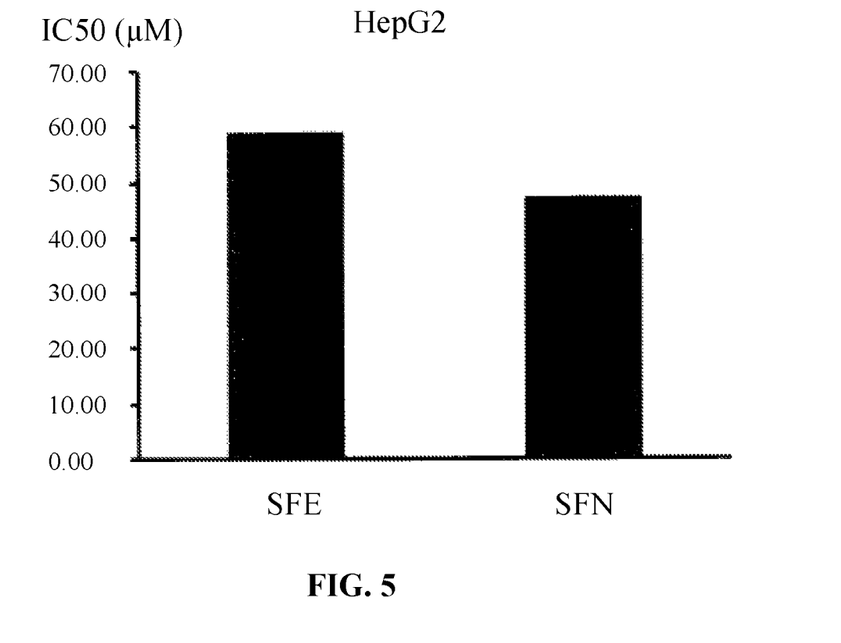
FIG. 5 shows comparison graphs of the half maximal inhibitory concentration (IC50) of sulforaphene and sulforaphane against human liver cancer cells HepG2.

It was indicated from FIG. 5 that sulforaphene has significant inhibition effect on the growth and proliferation of the human hepatocarcinoma cells HepG2. After 48 hrs of treatment, the IC50 of sulforaphene on the growth of the HepG2 cells was 59.0 μM. Sulforaphane has significant inhibition effect on the growth and proliferation of the human hepatocarcinoma cells HepG2. After 48 hrs of treatment, the IC50 of sulforaphane on the growth of the HepG2 cells was 47.33 μM.

Example 6

Materials and Methods

1. Experimental cell lines and related chemical reagents: human cervical carcinoma cell line HeLa purchased from US ATCC cell bank was cultured in the RPMI-1640 (Hy-Clone) culture medium comprising 10 v. % of the FBS, digested by the 0.25% trypsin solution and 0.02% EDTA solution, and then subcultured. All related chemical reagents in this experiment were purchased from Sigma.

2. Inhibition of HeLa cells in vitro by sulforaphene and sulforaphane: HeLa cells at exponential growth phase were collected, digested into single cells, and inoculated to 96-well plates with each hole containing 3000 cells. Then the 96-well plates were transferred into an incubator (37° C., 5% $CO_2$) for culture. Sulforaphene and sulforaphane were respectively dissolved by sterile deionized water, resulting solutions were then allowed to pass through 0.22 μM filters for removing bacteria. Filtrates were then diluted by a serum-containing medium to enable final concentrations of the sulforaphene or sulforaphane to be 10 μM, 20 μM, 30 μM, 40 μM, and 50 μM, respectively. After 24 hrs of cultivation, the HeLa cells were then cultured by the culture solutions comprising the sulforaphene or sulforaphane of corresponding concentrations, and to the culture media of the negative control group an equal volume of sterile deionized water was added for cell culture. After another 48 hrs of cultivation, 20 μL of MTT was added to each hole, and the plates were incubated for 3 hrs in the incubator (37° C., 5% $CO_2$). Solution in each hole was then removed and replaced by 150 μL of DMSO. Thereafter, the plates were cultured in a shaking table for 10 min, and the absorbance of each hole was measured at the wavelength of 490 nm. The number of viable cells in the negative control group at 0 hr was taken as a basis, and the IC 50 on the cell growth was calculated. The experiment results were listed in FIG. 6.

Experiment Results

Figure 6:
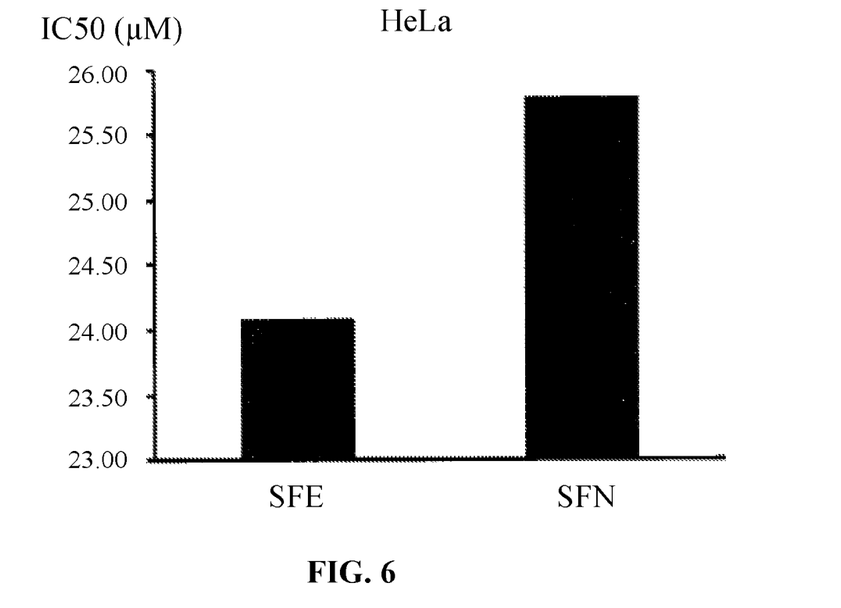
FIG. 6 shows comparison graphs of the half maximal inhibitory concentration (IC50) of sulforaphene and sulforaphane against human cervical cancer cells HeLa.

It was indicated from FIG. 6 that sulforaphene has significant inhibition effect on the growth and proliferation of the human cervical carcinoma cells HeLa. After 48 hrs of treatment, the IC50 of sulforaphene on the growth of the HeLa cells was 24.1 μM. Sulforaphane has significant inhibition effect on the growth and proliferation of the human cervical carcinoma cells HeLa. After 48 hrs of treatment, the IC50 of sulforaphane on the growth of the HeLa cells was 25.8 μM.

Example 7

Materials and Methods

1. Experimental cell lines and related chemical reagents: human malignant melanoma cell line A375 purchased from US ATCC cell bank was cultured in the RPMI-1640 (Hy-Clone) culture medium comprising 10 v. % of the FBS, digested by the 0.25% trypsin solution and 0.02% EDTA solution, and then subcultured. All related chemical reagents in this experiment were purchased from Sigma.

2. Inhibition of A375 cells in vitro by sulforaphene and sulforaphane: A375 cells at exponential growth phase were collected, digested into single cells, and inoculated to 96-well plates with each hole containing 3000 cells. Then the 96-well plates were transferred into an incubator (37° C., 5% $CO_2$) for culture. Sulforaphene and sulforaphane were respectively dissolved by sterile deionized water, resulting solutions were then allowed to pass through 0.22 µM filters for removing bacteria. Filtrates were then diluted by a serum-containing medium to enable final concentrations of the sulforaphene or sulforaphane to be 10 µM, 20 µM, 30 µM, 40 µM, and 50 µM, respectively. After 24 hrs of cultivation, the A375 cells were then cultured by the culture solutions comprising the sulforaphene or sulforaphane of corresponding concentrations, and to the culture media of the negative control group an equal volume of sterile deionized water was added for cell culture. After another 48 hrs of cultivation, 20 µL of MTT was added to each hole, and the plates were incubated for 3 hrs in the incubator (37° C., 5% $CO_2$). Solution in each hole was then removed and replaced by 150 µL of DMSO. Thereafter, the plates were cultured in a shaking table for 10 min, and the absorbance of each hole was measured at the wavelength of 490 nm. The number of viable cells in the negative control group at 0 hr was taken as a basis, and the IC 50 on the cell growth was calculated. The experiment results were listed in FIG. 7.

Experiment Results

Figure 7:
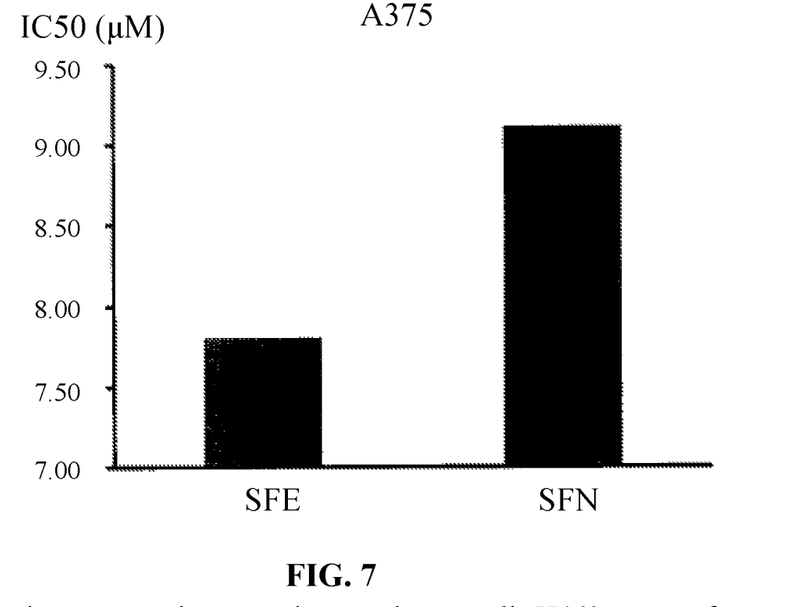
FIG. 7 shows comparison graphs of the half maximal inhibitory concentration (IC50) of sulforaphene and sulforaphane against human malignant melanoma cancer cells A375.

It was indicated from FIG. 7 that sulforaphene has significant inhibition effect on the growth and proliferation of the human malignant melanoma cells A375. After 48 hrs of treatment, the IC50 of sulforaphene on the growth of the A375 cells was 7.8 µM. Sulforaphane has significant inhibition effect on the growth and proliferation of the human malignant melanoma cells A375. After 48 hrs of treatment, the IC50 of sulforaphane on the growth of the A375 cells was 9.11 µM.

Example 8

Materials and Methods

Erlotinib, gemcitabine, paclitaxel, and 5-FU are four effective drugs for treating lung cancer and mammary cancer. As a drug for target therapy, the erlotinib is applicable to a third-line treatment of locally advanced or metastatic non-small cell lung cancer when two or more than two chemotherapies are failed. Currently, the gemcitabine is clinically utilized as the drug of the first-line therapy in treating advanced non-small cell lung cancer and the metastatic breast cancer. The paclitaxel is primarily applied in the mammary cancer and has a certain efficacy in treating the lung cancer as well. The 5-FU has relatively good efficacy in treating the mammary cancer and the digestive system cancer (esophageal cancer, stomach cancer, colon cancer, pancreatic cancer, and liver cancer). Thus, the above four drugs are selected as the chemotherapeutic drugs in the control groups to study the differences antitumor effects compared with the sulforaphene. 1. Experimental cell lines and related chemical reagents: sources and cultivation of the human lung adenocarcinoma cells A549, the human lung squamous carcinoma cell line H460, the human breast carcinoma cell line MCF-7 are described in the above. The related chemical reagents in the experiment are all purchased from Sigma 2 Inhibition of cells A549, H460, and MCF-7 in vitro by the sulforaphene and other chemotherapeutic drugs: cells A549, H460, and MCF-7 at exponential growth phase were collected, digested into single cells, and inoculated to 96-well plates with each hole containing 3000 cells. Then the 96-well plates were transferred into the incubator (37° C., 5% $CO_2$) for culture. The cells were respectively treated by 10 µM of the sulforaphene and 10 µM of other chemotherapeutic drugs (erlotinib, gemcitabine, paclitaxel, and 5-FU), cells in culture media of negative control groups were cultured by equal volume of sterile deionized water. The anti-tumor effects of the above drugs were measured by the MTT assay. The number of viable cells in the negative control groups at 0 hr was taken as a basis to calculate the anti-tumor effects. The inhibition rates of the drugs against the tumor cells were specifically listed in Table 1.

TABLE 1

| | Inhibition rate (%) of sulforaphene and contrast chemotherapeutic drugs | | | | |
|---|---|---|---|---|---|
| Cell line | Sulforaphene | Erlotinib | Gemcitabine | Paclitaxel | 5-FU |
| A549 | 46.8 | 30.3 | 6.9 | 28.8 | — |
| H460 | 34.2 | 33.1 | 4.3 | 17.3 | — |
| MCF-7 | 41.9 | NA | 40.1 | 89.6 | 15.8 |

It is known from the experiment results in Table 1 that compared with the erlotinib, the gemcitabine, and the paclitaxel, the sulforaphene has much significant inhibition effect against the growth and proliferation of cells A549 and H460. In cells MCF-7, the anti-tumor effect of the sulforaphene is not comparable with the paclitaxel of the same concentration but is significantly higher than the gemcitabine and the 5-FU.

Thus, the sulforaphene has comparable or much superior inhibition effect against most tumor cells compared with the sulforaphane and other third-line chemotherapeutic or targeting drugs, which include but are not limited to the erlotinib, the gemcitabine, and the paclitaxel. Thus, sulforaphene possesses significant inhibition effect on the growth of the following tumor cells, which include but are not limited to human lung adenocarcinoma, human lung squamous carcinoma, human pancreatic cancer, human liver cancer, human breast cancer, human cervical cancer, and human malignant melanoma.

II. Growth Inhibition of Animal Cancer Cells In Vivo

Example 9

1. Inoculation of tumor cells into armpit 1.1 Preparation of experimental animals: 30 nude mice with equal numbers of females and males were fed in normal conditions in the laboratory for between 3 and 5 days.

1.2. Preparation of H460 cells: H460 tumor cells were normally cultured, and diluted using the PBS so as to prepare a suspension of tumor cells having a concentration of $7.5 \times 10^6$ tumor cells per milliliter.

1.3 Inoculation of tumor cells: the suspension of the tumor cells was fully shaken and 0.2 mL of the suspension was then sucked by a sterile syringe having a capacity of 1 mL. The tumor cells were then inoculated into armpits of the nude mice via subcutaneous injection. The inoculated mice were then fed for between 2 and 3 days in normal conditions. When the tumor tissue grew to a size with a long axis of approximately 3 mm and a short axis of approximately 2 mm, all the nude mice having the tumor tissues were randomly divided into three groups, which were utilized in subsequent administration experiments.

2. Design of the experimental groups: an aqueous solution of an orally administered drug had a concentration of $35.37 \times 10^{-3}$ mol·$L^{-1}$;

2.1 Control group: five male mice and five female mice having tumor tissues were orally administered with ultrapure water for three times each week (respectively at Monday, Wednesday, and Friday afternoons), and the administered volume was 0.3 mL for each time.

2.2 Experimental group 1: five male mice and five female mice having tumor tissues were orally administered with sulforaphene with a dosage of 75 mg of the sulforaphene per kg of weight for three times each week (respectively at Monday, Wednesday, and Friday afternoons), and the administered volume was 0.3 mL for each time.

2.3 Experimental group 2: five male mice and five female mice having tumor tissues were orally administered with sulforaphane with a dosage of 75 mg of the sulforaphene per kg of weight for three times each week (respectively at Monday, Wednesday, and Friday afternoons), and the administered volume was 0.3 mL for each time.

3. Acquisition of experimental data 3.1 Acquisition of weight data of nude mice: weight data of the nude mice were collected three times per week (respectively at Monday, Wednesday, and Friday afternoons). An electronic balance was utilized to record the weight data, and an accuracy of the weight data was 0.01 g.

3.2. Acquisition of sizes of tumor tissues in the nude mice: the sizes of the tumor tissues in the nude mice were measured three times per week (respectively at Monday, Wednesday, and Friday afternoons). An electronic vernier caliper was utilized to measure the long axis and the short axis of the tumor tissues, and an accuracy of the data was 0.01 mm.

3.3. Observations of other data and phenomenon: the survival conditions of the nude mice were closely observed. In case of death, the time of death, the number of the nude mouse, and the corresponding group were timely recorded. And in case of abnormal conditions of the nude mice, the time of the occurrence and the symptoms were timely recorded.

3.4 Finish time of the experiments: when the tumor tissues in the nude mice of the control group reach an average size of 1000 mm$^3$ (Volume=long axis×short axis 2×0.5236), the weights and the sizes of the tumor tissues of the nude mice were recorded, and then the experiments were stopped and the nude mice were treated.

3.5 Treatment of nude mice when finishing the experiments: the nude mice were killed, arranged according to different groups, and photographed. Six representative mice were selected from each group and photographed. Then the tumor tissues were respectively isolated, weighed, placed at corresponding positions, and photographed. Experiment results were listed in Table 2:

TABLE 2

Tumor volumes of sulforaphene administered group, sulforaphane administered group, and negative control group

|  | Tumor volume on 1$^{st}$ day | Tumor volume on 3$^{rd}$ day | Tumor volume on 6$^{st}$ day | Tumor volume on 8$^{th}$ day | Tumor volume on 10$^{th}$ day |
|---|---|---|---|---|---|
| Negative control group (not administered with drugs) | 63.23745 | 159.603 | 413.2829 | 750.5499 | 1055.276 |
| Sulforaphene (75 mg/kg) | 35.99841 | 68.41752 | 217.957 | 336.6193 | 530.4369 |

TABLE 2-continued

Tumor volumes of sulforaphene administered group, sulforaphane administered group, and negative control group

|  | Tumor volume on 1$^{st}$ day | Tumor volume on 3$^{rd}$ day | Tumor volume on 6$^{st}$ day | Tumor volume on 8$^{th}$ day | Tumor volume on 10$^{th}$ day |
|---|---|---|---|---|---|
| Sulforaphane (75 mg/kg) | 30.55106 | 78.80789 | 257.8812 | 389.6022 | 552.7308 |

Figure 8:
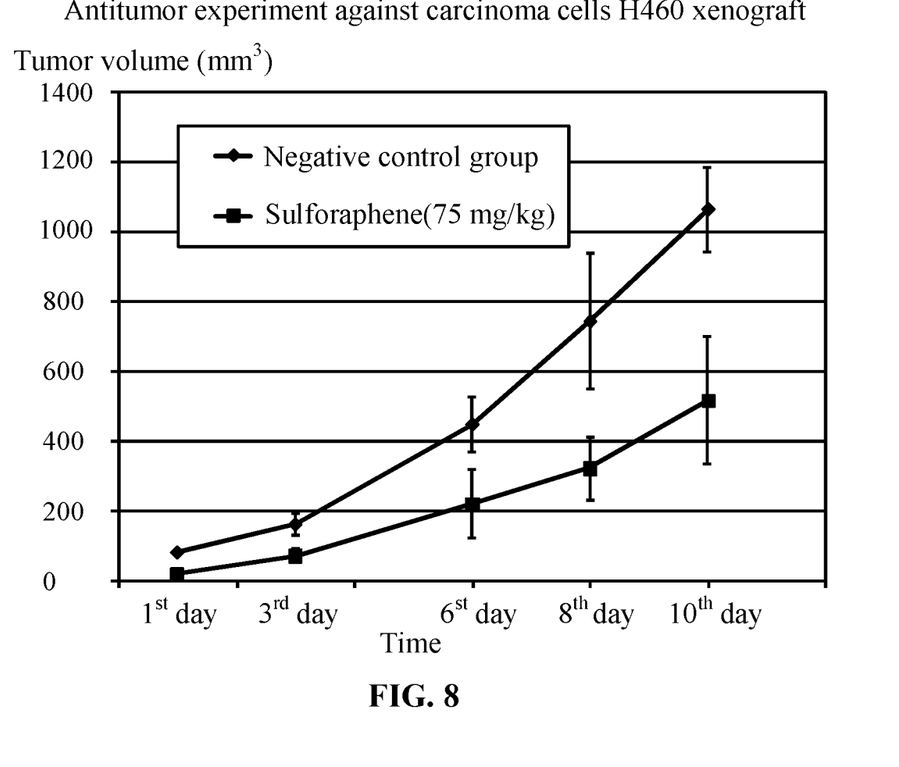
FIG. 8 shows antitumor results of sulforaphene against human lung squamous carcinoma cells H460 xenograft in nude mice.
Figure 9:
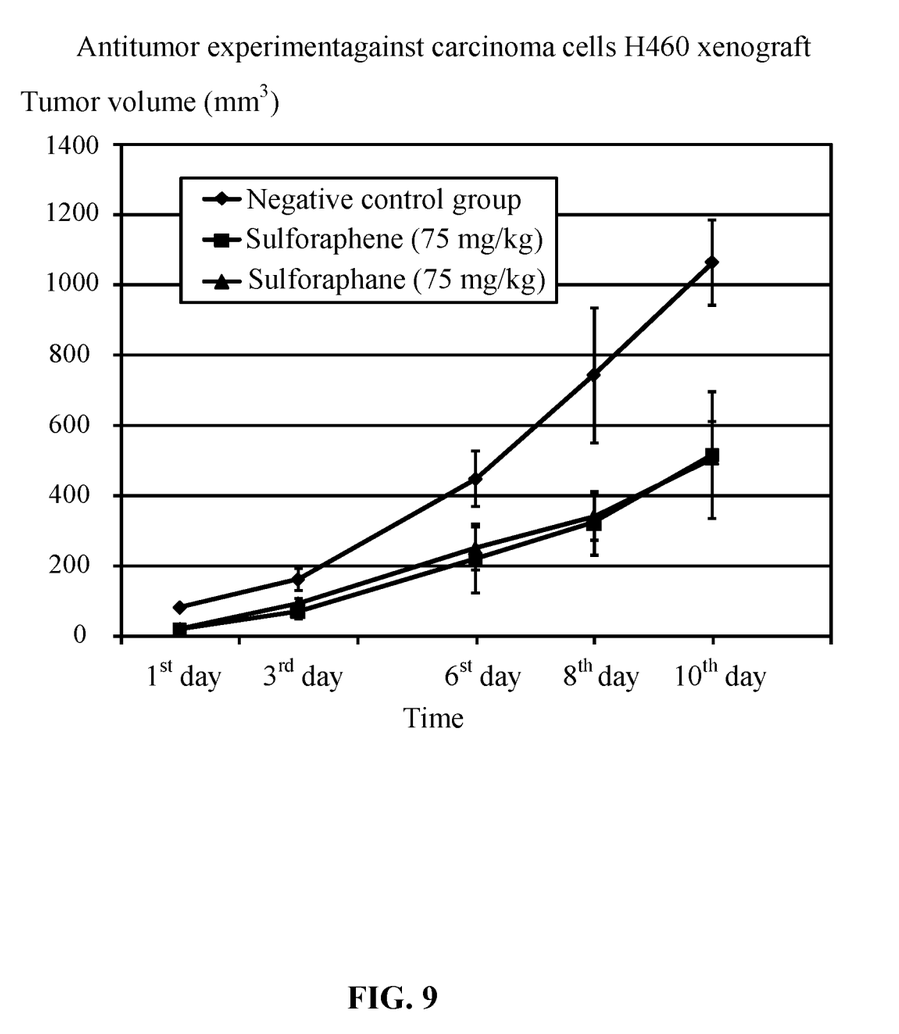
FIG. 9 shows antitumor results of sulforaphene and sulforaphane against human lung squamous carcinoma cells H460 xenograft in nude mice.

Each group of the nude mice was orally administered with the sulforaphene or drugs of the control groups (with 75 mg/kg each time). It is known from the above results that the sulforaphene has significant inhibition effect on the growth of the tumor cells in vivo (as shown in FIG. 8), and the inhibition effect of the sulforaphene is superior to that of the sulforaphane (as shown in FIG. 9).

III. Toxicity Experiment on Human Peripheral Blood Mononuclear Cell (PBMC)

General operations: normal peripheral blood cells were isolated by Ficoll to obtain mononuclear cells. The mononuclear cells were rinsed by the PBS for three times, and added with IMDM+10% FBS to prepare suspensions. 10 μM, 30 μM, and 50 μM of sulforaphene or sulforaphane and other four chemotherapeutic drugs were added to the suspensions for treatment, respectively. The suspensions were then inoculated into 96-well plates, with each hole containing 25 thousands cells per 100 μL of the culture medium, and cultured overnight at 37° C.

Treatment: because the proliferation of the PBMCs is very limited and the PBMCs quickly enter a decline phase. Thus, the cell viability was measured by the MTT assay after 24 hrs of culture. Four drugs with different mechanisms were employed to treat leukocytes, which were cis-platinum, 5-fluorouracil (5-FU), paclitaxel, and adriamycin, respectively, and a drug concentration of thereof was 10 μM. A total of eleven experiment groups were divided: sulforaphene treated groups with concentrations of 10 μM, 30 μM, and 50 μM, sulforaphane treated groups with concentrations of 10 μM, 30 μM, and 50 μM, a cis-platinum treated group, a paclitaxel treated group, an adriamycin treated group, a 5-FU treated group, and a negative control group, specific data of which are listed in Table 3. The group where PBMCs were treated by the sterile deionized water was selected as the negative control group.

TABLE 3

Experiment results of toxicity of sulforaphene, sulforaphane, and construct chemotherapeutic drugs on PBMCs

|  | 1 | 2 | 3 | 4 | Mean value | Cell viability (%) |
|---|---|---|---|---|---|---|
| 10 μM Sulforaphene | 0.886 | 0.833 | 0.824 | 0.763 | 0.827 | 103.5 |
| 30 μM Sulforaphene | 0.782 | 0.706 | 0.713 | 0.671 | 0.718 | 89.9 |
| 50 μM Sulforaphene | 0.718 | 0.685 | 0.674 | 0.661 | 0.685 | 85.7 |
| 10 μM Sulforaphane | 0.702 | 0.633 | 0.705 | 0.593 | 0.658 | 82.4 |
| 30 μM Sulforaphane | 0.655 | 0.616 | 0.58 | 0.628 | 0.620 | 77.6 |
| 50 μM Sulforaphane | 0.663 | 0.621 | 0.610 | 0.610 | 0.626 | 78.4 |
| Paclitaxel | 0.712 | 0.743 | 0.683 | 0.650 | 0.697 | 87.2 |
| Adriamycin | 0.482 | 0.482 | 0.496 | 0.530 | 0.498 | 62.3 |
| Cis-platinum | 0.470 | 0.518 | 0.530 | 0.482 | 0.500 | 62.6 |
| 5-FU | 0.493 | 0.484 | 0.525 | 0.461 | 0.491 | 61.4 |
| Negative control | 0.81 | 0.809 | 0.786 | 0.790 | 0.799 | 100 |

Example 10

Materials and Methods

1. Experimental cells: normal peripheral blood cells were isolated by Ficoll to obtain mononuclear cells. The mononuclear cells were rinsed by the PBS for three times, added with IMDM+10% FBS to prepare suspensions, commonly digested by 0.25% trypsin solution and 0.02% EDTA solution, and then subcultured.

2. Inhibition of PBMCs in vitro by sulforaphene and the contrast chemotherapeutic drugs: signal cells of the digested PBMCs were inoculated to the 96-well plates with each hole containing 3000 cells. Then the 96-well plates were transferred into an incubator at 37° C. for culture. The sulforaphene was dissolved by the sterile deionized water, and a resulting solution was then allowed to pass through a 0.22 μM filter for removing bacteria. A filtrate was thereafter diluted by a serum-containing medium to enable final concentrations of the sulforaphene to be 10 μM, 30 μM, and 50 μM, respectively. The sulforaphane was prepared in the same way. Concentrations of the contrast chemotherapeutic drugs were as follows: 50 μM of the cis-platinum, 60 μM of the 5-FU, 20 μM of the paclitaxel, 5 μM of the adriamycin. After 12 hrs of cultivation, the PBMCs were then cultured by culture solutions comprising the sulforaphene of corresponding concentrations, and to the culture media of the negative control group an equal volume of sterile deionized water was added for cell culture. After another 24 hrs of cultivation, 20 μL of MTT was added to each hole, and the plates were incubated for 3 hrs in the incubator (37° C., 5% $CO_2$). Solution in each hole was then removed and replaced by 150 μL of DMSO. Thereafter, the plates were cultured in a shaking table for 10 min, and the absorbance of each hole was measured at the wavelength of 490 nm Experiment results were listed in Table 3.

Experiment Results

It is indicated from Table 3 that the toxicity of the sulforaphene on the PBMCs is significantly lower than the sulforaphane and the other selected chemotherapeutic drug treated groups. The contrast chemotherapeutic drugs have significant inhibition effect on the growth and proliferation of the PBMCs. The sulforaphane has certain effect on the proliferation of the cells, while the effect of the sulforaphene on the proliferation of the cells is not significant.

IV. Toxicity Experiment on Rat Cardiomyocytes

General operations: 1-2 day old neonatal SD rats (female or male) were selected and cardiomyocytes were isolated in sterile condition. Cardiomyocytes were cultured for 3 days and then treated with sulforaphene or sulforaphane of concentrations of 10 μM, 30 μM, and 50 μM, or adriamycin of the concentration of 10 μM for 24 hrs. The cardiotoxicity of the above drugs were represented by a ratio of ATP/total protein. The experiment was performed in 8 groups: sulforaphene treated groups with concentrations of 10 μM, 30 μM, and 50 μM, sulforaphane treated groups with concentrations of 10 μM, 30 μM, and 50 μM, an adriamycin treated group, and a negative control group, specific data were listed in Table 3. The group where PBMCs were treated by the sterile deionized water was selected as the negative control group.

Example 11

Materials and Methods

1. Experimental cells: 1-2 day old neonatal SD rats (female or male) were selected and sterilized. Then ventricular muscles were collected and digested by trypsin to prepare cardiomyocyte suspensions. The suspensions were cultured in the incubator (37° C., 5% $CO_2$), and primary cardiomyocytes were cultured by differential adhesion. An average viability of the cardiomyocytes evaluated by Trypan blue staining was 98.2%, and a purity of the cardiomyocytes evaluated by immunofluorescence method is 98.7%.

2. Inhibition of the rat primary cardiomyocytes in vitro by sulforaphene and the contrast chemotherapeutic drugs: single cells of the digested rat primary cardiomyocytes were inoculated to 24-well plates and incubated in the incubator (37° C., 5% $CO_2$). The sulforaphene, the sulforaphane, and the adriamycin were prepared by the same methods as described in the above. After 12 hrs of cultivation, the rat primary cardiomyocytes were then cultured by culture solutions comprising the sulforaphene, the sulforaphane, or the adriamycin of corresponding concentrations, and to the culture media of the negative control group an equal volume of sterile deionized water was added for cell culture. After another 6 hrs of cultivation, the culture solution in each hole was replaced by the normal culture solution not containing any drugs, and incubated for 42 hrs in the incubator (37° C., 5% $CO_2$). Solution in each hole was then removed, and cells therein were rinsed by the PBS for three times, digested by the trypsin, and gathered into two parts. One part of the cells was utilized to measure the ATP level by the reporter gene assay, and the other part of the cells was utilized to measure the cellular protein concentration by BAC assay. The ratio of ATP (ng) to the protein concentration (μg) was calculated, and the ratio of each experimental group is divided by the ratio of the contrast group to obtain the relative ratio of ATP/total protein, experimental results were listed in Table 4.

TABLE 4

Experiment results of toxicity of sulforaphene, sulforaphane, and adriamycin on rat cardiomyocytes

|  | 1 | 2 | 3 | Mean value (%) |
|---|---|---|---|---|
| 10 μM Sulforaphene | 98.2 | 99.4 | 95.9 | 97.83 |
| 30 μM Sulforaphene | 94.1 | 95.5 | 93.2 | 94.27 |
| 50 μM Sulforaphene | 91.0 | 92.3 | 88.7 | 90.67 |
| 10 μM Sulforaphane | 90.0 | 88.2 | 91.4 | 89.87 |
| 30 μM Sulforaphane | 85.1 | 83.3 | 81.6 | 83.33 |
| 50 μM Sulforaphane | 77.5 | 76.7 | 73.9 | 76.03 |
| Adriamycin | 47.3 | 43.1 | 50.5 | 46.97 |

Experiment Results

It is known in Table 4 that the toxicity of the sulforaphene on the cardiomyocytes is significantly lower than that of the sulforaphane, and the Adriamycin has obvious toxicity on the cardiomyocytes.

Conclusion: it is indicated from the systematic study of the invention that sulforaphene is superior to conventional antitumor drugs including sulforaphane, erlotinib, gemcitabine, and paclitaxel in inhibiting the growth of many kinds of cancer cells, and has higher security than sulforaphane, cis-platinum, 5-fluorouraeil, paclitaxel, and adriamycin. So, sulforaphene has potential antitumor activities against lung cancer, lung squamous cell carcinoma, pancreas cancer, liver cancer, mammary cancer, cervical carcinoma, malignant melanoma, and so on.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method of treating human or mammalian cancer, the method comprising administering to a patient or a mammal in need thereof a pharmaceutical composition, health product, or food additive comprising 1-(alkylsulfinyl)-2-isothiocyanatoalkyl-1-alkene having formula I, wherein
- $R_1$ is a methyl;
- $R_2$ and $R_3$ at each occurrence independently represent hydrogen, a substituted or unsubstituted alkyl, vinyl, alkynyl, aryl, alkoxy, epoxy group, heterocyclic nitrogen and aryloxy;
- $R_4$ is a substituted or unsubstituted alkylidene, —$CH_2$—O—$CH_2$—, and alkoxyl aryl; and
- n is an integer from 1 to 10; and
- the cancer is liver cancer, lung cancer, mammary cancer, pancreatic cancer, cervical carcinoma, or malignant melanoma.

2. The method of claim 1, wherein $R_2$ and $R_3$ both are hydrogen.

3. The method of claim 1, wherein $R_4$ is a methylene and n=2.

4. The method of claim 1, wherein the formula I is sulforaphene with a chemical name of 4-isothiocyanato-1-(methylsulfinyl)-1-butene.

5. The method of claim 4, wherein sulforaphene is extracted from radish seeds, radish seedlings, or radish.

6. The method of claim 1, wherein the pharmaceutical composition, health product, and food additive comprise a pharmaceutically acceptable carrier, an additive, and a pharmaceutically acceptable excipient.

7. The method of claim 4, wherein the pharmaceutical composition, health product, and food additive comprise a pharmaceutically acceptable carrier, an additive, and a pharmaceutically acceptable excipient.

8. A method of treating human or mammalian cancer, the method comprising administering to a patient or a mammal in need thereof 1-(alkylsulfinyl)-2-isothiocyanatoalkyl-1-alkene having the formula I wherein the cancer is liver cancer, lung cancer, mammary cancer, pancreatic cancer, cervical carcinoma, or malignant melanoma.

9. The method of claim 1, wherein the administering is oral, nasal, parenteral, topical, or transdermal.

10. The method of claim 9, wherein the parenteral administration is by intravenous injection, intramuscular injection, intrasternal injection, hypodermic injection, or intra-articular injection.

11. A method of treating human or mammalian cancer, the method comprising administering to a patient or a mammal in need thereof a pharmaceutical composition, health product, or food additive comprising 1-(alkylsulfinyl)-2-isothiocyanatoalkyl-1-alkene having formula I, wherein
- $R_1$ is a methyl;
- $R_2$ and $R_3$ at each occurrence independently represent a substituted or unsubstituted alkyl, vinyl, alkynyl, aryl, alkoxy, epoxy group, heterocyclic nitrogen and aryloxy;
- $R_4$ is a substituted or unsubstituted —$CH_2$—O—$CH_2$—, and alkoxyl aryl; and
- n is an integer from 1 to 10; and
- the cancer is liver cancer, lung cancer, mammary cancer, pancreatic cancer, cervical carcinoma, or malignant melanoma.

12. The method of claim 11, wherein the administering is oral, nasal, parenteral, topical, or transdermal.

13. The method of claim 12, wherein the parenteral administration is by intravenous injection, intramuscular injection, intrasternal injection, hypodermic injection, or intra-articular injection.

* * * * *